US008105604B2

(12) United States Patent
    Sugiyama

(10) Patent No.: US 8,105,604 B2
(45) Date of Patent: Jan. 31, 2012

(54) WT1 MODIFIED PEPTIDE

(75) Inventor: Haruo Sugiyama, Minoo (JP)

(73) Assignee: International Institute of Cancer Immunology, Inc., Suita-shi (JP)

( * ) Notice: Subject to any disclaimer, the term of this patent is extended or adjusted under 35 U.S.C. 154(b) by 13 days.

(21) Appl. No.: 12/552,660

(22) Filed: Sep. 2, 2009

(65) Prior Publication Data

US 2009/0325886 A1    Dec. 31, 2009

Related U.S. Application Data

(63) Continuation of application No. 10/471,835, filed as application No. PCT/JP02/02794 on Mar. 22, 2002, now abandoned.

(30) Foreign Application Priority Data

Mar. 22, 2001    (JP) .................................. 2001-083250

(51) Int. Cl.
    *A61K 39/00*    (2006.01)
    *A61K 39/38*    (2006.01)
    *A61K 38/08*    (2006.01)
(52) U.S. Cl. .................. 424/185.1; 424/184.1; 514/21.6
(58) Field of Classification Search .................. None
    See application file for complete search history.

(56) References Cited

U.S. PATENT DOCUMENTS

| | | | |
|---|---|---|---|
| 6,034,235 | A | 3/2000 | Sugiyama et al. |
| 6,207,880 | B1 | 3/2001 | Kossmann et al. |
| 7,030,212 | B1 | 4/2006 | Sugiyama et al. |
| 7,342,092 | B2 | 3/2008 | Sugiyama |
| 7,378,384 | B2 | 5/2008 | Sugiyama et al. |
| 7,390,871 | B2 | 6/2008 | Sugiyama et al. |
| 7,420,034 | B2 | 9/2008 | Sugiyama et al. |
| 7,517,950 | B2 | 4/2009 | Sugiyama et al. |
| 2003/0039635 | A1 | 2/2003 | Gaiger et al. |
| 2003/0072767 | A1 | 4/2003 | Gaiger et al. |
| 2003/0082196 | A1 | 5/2003 | Gaiger et al. |
| 2003/0092656 | A1 | 5/2003 | Sugiyama |
| 2003/0095971 | A1 | 5/2003 | Gaiger et al. |
| 2003/0198622 | A1 | 10/2003 | Gaiger et al. |
| 2003/0215458 | A1 | 11/2003 | Gaiger et al. |
| 2003/0235557 | A1 | 12/2003 | Gaiger et al. |
| 2004/0018204 | A1 | 1/2004 | Gaiger et al. |
| 2004/0097703 | A1 | 5/2004 | Sugiyama |
| 2004/0126362 | A1 | 7/2004 | Gaiger et al. |
| 2004/0247609 | A1 | 12/2004 | Sugiyama |
| 2005/0002951 | A1 | 1/2005 | Sugiyama et al. |
| 2006/0217297 | A1 | 9/2006 | Sugiyama et al. |
| 2007/0128207 | A1 | 6/2007 | Sugiyama |
| 2008/0070835 | A1 | 3/2008 | Sugiyama |
| 2008/0152631 | A1 | 6/2008 | Sugiyama |
| 2009/0099090 | A1 | 4/2009 | Sugiyama et al. |
| 2009/0143291 | A1 | 6/2009 | Sugiyama et al. |

FOREIGN PATENT DOCUMENTS

| | | |
|---|---|---|
| EP | 1 004 319 | 7/1998 |
| EP | 1 103 564 | 7/1999 |
| EP | 1 074 267 | 7/2000 |
| JP | 61-22018 | 1/1986 |
| JP | 9-104629 | 4/1997 |
| JP | 2001-89389 | 4/2001 |
| WO | WO 91/07509 | 5/1991 |
| WO | WO 95/16464 | 6/1995 |
| WO | WO 95/29995 | 11/1995 |
| WO | WO 96/02555 | 2/1996 |
| WO | WO 99/44634 | 9/1999 |
| WO | WO 00/18795 | 4/2000 |
| WO | WO 00/26249 | 5/2000 |
| WO | WO 00/41463 | 7/2000 |
| WO | WO 00/44349 | 8/2000 |
| WO | WO 01/62920 | 8/2001 |
| WO | WO 02/079253 | 10/2002 |
| WO | WO 03/028758 | 4/2003 |
| WO | WO 03/106682 | 12/2003 |

OTHER PUBLICATIONS

Ezzell. Cancer "Vaccines": an idea whose time has come? Journal of of NIH Research, 1995. vol. 7, pp. 46-49.*
Forni, Lollini, Musiani, and Colombo. Immunoprevention of cancer: is the time ripe? Cancer Research, 2000. vol. 60, pp. 2571-2575.*
Donnelly. Cancer vaccine targets leukemia. Nature Medicine, 2003. vol. 9, pp. 1354-1356.*
De Gruijl and Curiel. Cancer vaccine strategies get bigger and better. Nature Medicine, 1999. vol. 5, pp. 1124-1125.*
Chatterjee, Foon, and Kohler. Idiotypic antibody immunotherapy of cancer. Cancer Immunol Immunother, 1994. vol. 38, pp. 75-82.*
Bodey, Bodey, Siegel, and Kaiser. Failure of cancer vaccines: the significant limitations of this approach to immunotherapy. Anticancer Research, 2000. vol. 20, pp. 2665-2676.*
Lee, Wang, Nielsen, Wunderlich, Migueles, Connors, Steinberg, Rosenberg, and Marincola. Increased vaccine-specific T cell frequency after peptide-based vaccination correlates with increased susceptibility to in vitro stimulation but does not lead to tumor regression. Journal of Immunology, 1999. vol. 163, pp. 6292-6300.*
Y. Oka, et al., "Cancer Immunotherapy Targeting Wilms' Tumor Gene WT! Product", J. Immunol., 2000, vol. 164, pp. 1887-1880.
U.S. Appl. No. 11/196,452, filed Aug. 4, 2005, Sugiyama, et al.
U.S. Appl. No. 11/953,281, filed Dec. 10, 2007, Sugiyama.
U.S. Appl. No. 12/095,418, filed May 29, 2008, Nishihara, et al.
U.S. Appl. No. 12/366,200, filed Feb. 5, 2009, Sugiyama, et al.
U.S. Appl. No. 12/552,660, filed Sep. 2, 2009, Sugiyama.
B. Palermo, et al., "Cytotoxic T-lymphocyte responses in melanoma through in vitro stimulation with the Melan-A peptide analogue A27L: a Qualitative Analysis", Melanoma Research, 2002, 12, pp. 491-498.

(Continued)

*Primary Examiner* — Anne M. Gussow
(74) *Attorney, Agent, or Firm* — Oblon, Spivak, McClelland, Maier & Neustadt, L.L.P.

(57) ABSTRACT

The present invention discloses a cancer antigen peptide comprising the following amino acid sequence: Cys Tyr Thr Trp Asn Gln Met Asn Leu (Sequence ID No. 3), a cancer vaccine having this for its active ingredient, and a DNA vaccine having for its active ingredient DNA that codes for this peptide.

5 Claims, 5 Drawing Sheets

OTHER PUBLICATIONS

H. Rammensee, et al., "MHC Ligands and Peptide Motifs: First Lisitng", Immunogenetics, 1995, 41: pp. 178-228.

N. Renkvist, et al., "A Listing of Human Tumor Antigens Recognized by T Cells", Cancer Immunol. Immunother, 2001, 50: pp. 3-15.

M. Gessler, et al., "Homozygous Deletion in Wilms Tumours of a Zinc-Finger Gene Identified by Chromosome", Nature, vol. 343, Feb. 22, 1990, pp. 774-778.

Y. Oka, et al., "Human Cytotoxic T-Lymphocyte Responses Specific for Peptides of the Wild-Type Wilms' Tumor Gene (WT1) Product", Immunogenetics, 2000, 51: pp. 99-107.

L. Gao, et al, "Selective Elimination of Leukemic CD34+ Progenitor Cells by Cytotoxic T Lymphocytes Specific for WT1", Blood, Apr. 1, 2000, vol. 95, No. 7, pp. 2198-2203.

A. Tsuboi, et al., "Cytotoxic T-Lymphocyte Responses Elicited to Wilms' Tumor Gene WT1 Product by DNA Vaccination", Journal of Clinical Immunology, vol. 20, No. 3, 2000, pp. 195-202.

A. Gaiger, et al., "Immunity of WT1 in the Animal Model and in Patients with Acute Myeloid Leukemia", Aug. 15, 2000, vol. 96, No. 4, pp. 1480-1489.

C. Melief, et al., "Potential Immunogenicity of Oncogene and Tumor Suppressor Gene Products", Currentent Opinion in Immunology, 1993, 5: pp. 709-713.

E. Ribi, et al., "Factors Influencing Protection Against Experimental Tuberculosis in Mice by Heat-Stable Cell Wall Vaccines", Journal of Bacteriology, Oct. 1966, vol. 92, No. 4, pp. 869-879.

F. Nestle, et al., Vaccination of Melanoma Patients with Peptide- or Tumor Lysate-Pulsed Dendritic Cells, Nature Medicine, vol. 4, No. 3, Mar. 1998, pp. 328-332.

L. Chedid, et al., Protective Effect of Delipidated Mycobacterial Cells and Purified Cell Walls Against Ehrlich Carcinoma and a Syngeneic Lymphoid Leukemia in Mice[1], Cancer Research, 33, Sep. 1973, pp. 2187-2195.

XP-002961732, A. Tsuboi, et al., "Enhanced Induction of Human WT1-Specific Cytotoxic T-lymphocytes with a 9-mer WT1 Peptide Modified at HLA-A*2402-Binding Residues", Springer-Verlag 2002, p. 1-6.

A. Tsuboi, et al., "Enhanced WT1-Specific CTL Inducing Activity of Human WT1 Modified Peptide", The 31st Annual Meeting of the Japanese Society for Immunology, Dec. 11-13, 2001. (English translation of previously filed reference).

H. Sugiyama, "Wilms' Tumor Gene WT1: Its Oncogenic Function and Clinical Application", International Journal of Hematology, vol. 73, 2001, pp. 177-187.

R. Lin, et al., "Present Status of the Use of Cytokines as Adjuvants with Vaccines to Protect Against infectious Diseases", Clin. Infect. Dis., vol. 21, No. 6, 1995, pp. 1439-1449.

Y. Tanio, Partial Englis Translation of Japanese Journal of Cancer and Chemotherapy, vol. 7, No. 9, pp. 1710-1718, 1980.

T. Azuma, et al., "Identification of a Novel WT1-Derived Peptide Which Induces Human Leucocyte Antigen-A24-Restricted Anti-Leukaemia Cytotoxic T Lymphocytes", British Journal of Haematology, 2002, 116, pp. 601-603.

S. Rosenberg, et al., "A New Era for Cancer Immunotherapy Based on the Genes that Encode Cancer Antigens", Immunity, vol. 10, pp. 281-287, Mar. 1999.

A. Bakker, et al., Melanocyte Lineage-Specific Antigen gp100 is Recognized by Melanoma-Derived Tumor-Infiltrating Lymphocytes, The Journal of Experimental Medicine, vol. 179, Mar. 1994, pp. 1005-1009.

Y. Kawakami, et al., "Cloning of the Gene Coding for a Shared Human Melanoma Antigen Recognized by Autologous T Cells Infiltrating into Tumor", Proc. Natil. Acad. Sci., USA, vol. 91, pp. 3515-3519, Apr. 1994.

V. Brichard, et al., "The Tyrosinase Gene Codes for an Antigen Recognized by Autologous Cytolytic T Lymphocytes on HLA-A2 Melanomas", Journal of Experimental Medicine, vol. 178, Aug. 1993, pp. 489-495.

B. Fisk, et al., "Identification of an Immunodominant Peptide of HER-2/neu Protooncogene Recognized by Ovarian Tumor-specific Cytotoxic T Lymphocyte Lines", Journal of Experimental Medicine, vol. 181, Jun. 1995, pp. 2109-2117.

K. Tsang, et al., "Generation of Human Cytotoxic T Cells Specific for Human Carcinoembryonic Antigen Epitopes from Patients Immunized with Recombinant Vaccinia-CEA Vaccine", Journal of the National Cancer Institute, vol. 87, No. 13, Jul. 5, 1995, pp. 982-990.

P. Correale, et al., "In Vitro Generation of Human Cytotoxic T Lymphocytes Specific for Peptides Derived from Prostate-Specific Antigen", Journal of the National Cancer Institute, vol. 89, No. 4, Feb. 19, 1997.

K. Call, et al., "Isolation and Characterization of a Zinc Finger Polypeptide Gene at the Human Chromosome 11 Wilms' Tumor Locus", Cell, vol. 60, Feb. 9, 1990, pp. 509-520.

D. Pardoll, "New Strategies for Enhancing the Immunogencity of Tumors", Opinion in Immunology, 1993, 5: pp. 719-725.

N. Nanda, et al., "Induction of Anti-Self-Immunity to Cure Cancer", Cell, vol. 82, Jul. 14, 1995, pp. 13-17.

C. Melief, et al., "T-Cell Immunotherapy of Tumors by Adoptive Transfer of Cytotoxic T Lymphocytes and by Vaccination wit Minimal Essential Epitopes", Immunological Reviews, 1995, No. 146, pp. 167-177.

A. Gaiger, et al., "WT1: A New Leukemia and Cancer Antigen", Proceeding of the American Association for Cancer Research Annual Meeting, vol. 40, Mar. 1999, p. 424, #2802.

A. Buckler, et al., "Isolation, Characterization, and Expression for the Murine Wilms' Tumor Gene (WT1) During Kidney Development", Molecular and Cellular Biology, vol. 11, No. 3, 1991, pp. 1707-1712.

Y. Oka, et al., Hematology Frontier, 2000, vol. 10, No. 8, pp. 1017-1023, "3. Men'eki Ryoho 2) WT1 o Hyoteki to shita Hakketsubyo ni Taisuru Tokuiteki Men'eki Ryoho".

Y. Tanio, et al, Japanese Journ. of Cancer & Chemotherapy, 1980, vol. 7, No. 9, pp. 1710-1718, "Men'eki Kyoka Busshitsu".

Y. Oka, et al., "Induction of WT1 (Wilms' Tumor Gene)-Specific Cytotoxic T Lymphocytes by WT1 Peptide Vaccine and the Resultant Cancer Regression", PNAS, Sep. 21, 2004, vol. 101, No. 38, pp. 13885-13890.

Chinese Office Action dated Feb. 25, 2005.

S. Rosenberge, et al., "Immunologic and Therapeutic Evaluation of a Synthetic Peptide Vaccine for the Treatment of Patients with Metastatic Melanoma", Nature Medicine, vol. 4, No. 3, pp. 321-327, Mar. 1998.

"Complete Remission in a Patient with Recurrent Acute Myeloid Leukemia Induced by Vaccination with WT1 Peptide in the Absence of Hematological or Renal Toxicity", Leukemia (2004), vol. 18, pp. 165-166.

I. Higashi, Biomedicine & Therapeutics, 1988, vol. 20, No. 1, pp. 21-26, "BRM to shite no Saikin Kintai Seibun".

B. Zbar, et al., "Tumor Suppression by Cell Walls of Mycobacterium Bovis Attached to Oil Droplets[1]", Journal of the National Cancer Institute, vol. 48, No. 3, Mar. 1972, pp. 831-835.

M. Singh, et al., "Advances in Vaccine Adjuvants", Nature Biotechnology, vol. 17, Nov. 17, 1999, pp. 1075-1081.

U.S. Appl. No. 12/554,151, filed Sep. 4, 2009, Sugiyama.
U.S. Appl. No. 12/280,268, filed Aug. 21, 2008, Sugiyama.
U.S. Appl. No. 12/521,533, filed Jun. 26, 2009, Sugiyama.
U.S. Appl. No. 12/449,765, filed Aug. 26, 2009, Sugiyama.
U.S. Appl. No. 12/529,701, filed Sep. 2, 2009, Sugiyama.

Y. Oka, et al., "Cancer Immunotherapy Targeting Wilms' Tumor Gene WT! Product", J. Immunol., 2000, vol. 164, pp. 1883-1880.

K. Tadokoro, "Gan Yokusei Idenshi WT1 no Kino Hatsugen", Gendai Kagaku extra issue 33, "Gan Idenshi Kenkyu no Tenbo II", 1997, pp. 92-98.

* cited by examiner

SEQUENCE LISTING

<160> NUMBER OF SEQ ID NOS: 4

<210> SEQ ID NO 1
<211> LENGTH: 449
<212> TYPE: PRT
<213> ORGANISM: Mouse

```
<400> SEQUENCE: 1

Met Gly Ser Asp Val Arg Asp Leu Asn Ala Leu Leu Pro Ala Val Ser
                 5                  10                  15

Ser Leu Gly Gly Gly Gly Gly Cys Gly Leu Pro Val Ser Gly Ala
             20                  25                  30

Arg Gln Trp Ala Pro Val Leu Asp Phe Ala Pro Pro Gly Ala Ser Ala
             35                  40                  45

Tyr Gly Ser Leu Gly Gly Pro Ala Pro Pro Ala Pro Pro Pro
             50                  55                  60

Pro Pro Pro Pro His Ser Phe Ile Lys Gln Glu Pro Ser Trp Gly Gly
 65                  70                  75                  80

Ala Glu Pro His Glu Glu Gln Cys Leu Ser Ala Phe Thr Leu His Phe
                 85                  90                  95

Ser Gly Gln Phe Thr Gly Thr Ala Gly Ala Cys Arg Tyr Gly Pro Phe
                100                 105                 110

Gly Pro Pro Pro Pro Ser Gln Ala Ser Ser Gly Gln Ala Arg Met Phe
                115                 120                 125

Pro Asn Ala Pro Tyr Leu Pro Ser Cys Leu Glu Ser Gln Pro Thr Ile
130                 135                 140

Arg Asn Gln Gly Tyr Ser Thr Val Thr Phe Asp Gly Ala Pro Ser Tyr
145                 150                 155                 160

Gly His Thr Pro Ser His His Ala Ala Gln Phe Pro Gln His Ser Phe
                165                 170                 175

Lys His Glu Asp Pro Met Gly Gln Gln Gly Ser Leu Gly Glu Gln Gln
                180                 185                 190

Tyr Ser Val Pro Pro Pro Val Tyr Gly Cys His Thr Pro Thr Asp Ser
                195                 200                 205

Cys Thr Gly Ser Gln Ala Leu Leu Leu Arg Thr Pro Tyr Ser Ser Asp
210                 215                 220

Asn Leu Tyr Gln Met Thr Ser Gln Leu Glu Cys Met Thr Trp Asn Gln
225                 230                 235                 240

Met Asn Leu Gly Ala Thr Leu Lys Gly Met Ala Ala Gly Ser Ser Ser
                245                 250                 255

Ser Val Lys Trp Thr Glu Gly Gln Ser Asn His Gly Ile Gly Tyr Glu
                260                 265                 270

Ser Glu Asn His Thr Ala Pro Ile Leu Cys Gly Ala Gln Tyr Arg Ile
                275                 280                 285

His Thr His Gly Val Phe Arg Gly Ile Gln Asp Val Arg Arg Val Ser
                290                 295                 300

Gly Val Ala Pro Thr Leu Val Arg Ser Ala Ser Glu Thr Ser Glu Lys
305                 310                 315                 320

Arg Pro Phe Met Cys Ala Tyr Pro Gly Cys Asn Lys Arg Tyr Phe Lys
                325                 330                 335

Leu Ser His Leu Gln Met His Ser Arg Lys His Thr Gly Glu Lys Pro
                340                 345                 350

Tyr Gln Cys Asp Phe Lys Asp Cys Glu Arg Arg Phe Ser Arg Ser Asp
                355                 360                 365

Gln Leu Lys Arg His Gln Arg Arg His Thr Gly Val Lys Pro Phe Gln
                370                 375                 380

Cys Lys Thr Cys Gln Arg Lys Phe Ser Arg Ser Asp His Leu Lys Thr
385                 390                 395                 400

His Thr Arg Thr His Thr Gly Lys Thr Ser Glu Lys Pro Phe Ser Cys
                405                 410                 415
```

```
Arg Trp His Ser Cys Gln Lys Lys Phe Ala Arg Ser Asp Glu Leu Val
        420                 425                 430

Arg His His Asn Met His Gln Arg Asn Met Thr Lys Leu His Val Ala
        435                 440                 445

Leu
449

<210> SEQ ID NO 2
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 2

Cys Met Thr Trp Asn Gln Met Asn Leu
 1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 3

Cys Tyr Thr Trp Asn Gln Met Asn Leu
 1               5

<210> SEQ ID NO 4
<211> LENGTH: 9
<212> TYPE: PRT
<213> ORGANISM: Artificial Sequence
<220> FEATURE:
<221> NAME/KEY:
<222> LOCATION:
<223> OTHER INFORMATION: Antigenic Peptide

<400> SEQUENCE: 4

Ala Tyr Gly Leu Asp Phe Tyr Ile Leu
 1               5
```

WT1 MODIFIED PEPTIDE

This application is a Continuation of U.S. application Ser. No. 10/471,835, filed on Sep. 15, 2003, abandoned, which is the National Stage of PCT/JP02/02794, filed on Mar. 22, 2002.

TECHNICAL FIELD

The present invention relates to a cancer antigen based on the product of Wilms' tumor suppresser gene WT1. This cancer antigen is useful as an anticancer vaccine against cancers of the blood such as leukemia, myelodysplastic syndrome, multiple myeloma and malignant lymphoma, solid cancers such as gastric cancer, colon cancer, lung cancer, breast cancer, germinal cell cancer, liver cancer, skin cancer, bladder cancer, prostate cancer, uterine cancer, cervical carcinoma and ovarian cancer, as well as any cancer that expresses WT1.

DESCRIPTION OF THE RELATED ART

The immune mechanism for eliminating foreign objects from the body generally consists of humoral immunity, in which is involved macrophages that function as antigen-presenting cells that recognize an antigen, helper T-cells that activate other T-cells by recognizing antigens presented by said macrophages and producing various lymphokines, and B lymphocytes that differentiate into antibody-producing cells due to the action of said lymphokines; and, cellular immunity, by which killer T-cells (cytotoxic T-cells (CTL)), which have differentiated as a result of being presented with an antigen, attack and destroy target cells.

At present, cancer immunity is thought to mainly be the result of cellular immunity involving killer T-cells. In cancer immunity affected by killer T-cells, precursor T-cells, which have recognized cancer antigen presented in the form of a complex of major histocompatibility complex (MHC) class I (MHC class I antigen, also referred to as HLA antigen in the case of humans) and cancer antigen, differentiate and proliferate, and the resulting killer T-cells that have formed attack and destroy the cancer cells. At this time, the cancer cells present a complex of MHC class I antigen and cancer antigen on their cell surface, and this is targeted by the killer T-cells (Cur. Opin. Immunol., 5, 709, 1993; Cur. Opin. Immunol., 5, 719, 1993; Cell, 82, 13, 1995; Immunol. Rev., 146, 167, 1995).

The aforementioned cancer antigen presented by MHC class I antigen on the cancer cells serving as the target cells is thought to be a peptide composed of about 8-12 amino acids formed as a result of antigen protein synthesized within cancer cells being processed by intracellular protease (Cur. Opin. Immunol., 5, 709, 1993; Cur. Opin. Immunol., 5, 719, 1993; Cell, 82, 13, 1995; Immunol. Rev., 146, 167, 1995).

At present, although searches have been conducted for antigen proteins for various cancers, few have been verified to be cancer-specific antigens.

The tumor suppresser gene WT1 of Wilms tumor (WT1 gene) has been isolated from chromosome 11p13 as one of the causative genes of Wilms tumor based on analysis of the WAGR syndrome that occurs as a complication of Wilms tumor, aniridia, urogenital abnormalities, mental retardation and so forth (Gessler, M., et al., Nature, Vol. 343, p. 774-778 (1990)). Its genomic DNA is about 50 kb and is composed of 10 exons, while its cDNA is about 3 kb. The amino acid sequence estimated from cDNA is as shown in Sequence ID No. 1 (Mol. Cell. Biol., 11, 1707, 1991).

The WT1 gene is expressed with high frequency in human leukemia, and when leukemia cells are treated with WT1 antisense oligomer, the growth of the cells is inhibited (Japanese Unexamined Patent Publication No. 9-104627). Thus, WT1 gene is thought to act to promote the growth of leukemia cells. Moreover, WT1 is also highly expressed in solid cancers such as gastric cancer, colon cancer, lung cancer, breast cancer, germinal cell cancer, liver cancer, skin cancer, bladder cancer, prostate cancer, uterine cancer, cervical carcinoma and ovarian cancer (Japanese Patent Application No. 9-191635), and the WT1 gene has been demonstrated to be a novel tumor marker in leukemia and solid cancers.

Several cancer-specific antigen peptides consisting of a portion of the WT1 gene expression product are described in WO 00/06602, one particularly promising peptide is designated as $D^b$, and the following amino acid sequence: Cys Met Thr Trp Asn Gln Met Asn Leu (Sequence ID No. 2) (referred to as "WT1 wild peptide" in the present invention) is described therein.

DISCLOSURE OF THE INVENTION

Thus, an object of the present invention is to provide a peptide that is promising as a cancer vaccine and which has higher activity than previously known cancer-specific antigen peptides.

As a result of earnestly conducting various studies to solve the above problems, the inventors of the present invention found that a peptide (referred to as "WT1 modified peptide") having an amino acid sequence in which the second amino acid Met of the aforementioned known amino acid sequence (Sequence ID No. 2) is changed to Tyr, namely Cys Tyr Thr Trp Asn Gln Met Asn Leu (Sequence ID No. 3), has higher activity, thereby leading to completion of the present invention.

Thus, the present invention provides a peptide (WT1 modified peptide) consisting of 9-30 amino acids and comprising the following amino acid sequence: Cys Tyr Thr Trp Asn Gln Met Asn Leu (Sequence ID No. 3). This peptide is preferably a polypeptide consisting of 9-12 amino acids and comprising the amino acid sequence indicated in Sequence ID No. 3 and, more preferably, a peptide consisting of the amino acid sequence indicated in Sequence ID No. 3.

Moreover, the present invention provides a cancer vaccine having for its active ingredient the aforementioned WT1 modified peptide.

Moreover, the present invention also provides a DNA vaccine against cancer having for its active ingredient DNA coding for the aforementioned peptide.

In addition, the present invention provides antigen-presenting cells on which presented a complex of HLA antigen (MHC class I antigen) and the aforementioned peptide.

Moreover, the present invention also provides cytotoxic T-cells that recognize a complex of HLA antigen and the aforementioned peptide.

DESCRIPTION OF THE PREFERRED EMBODIMENTS

Figure 1:
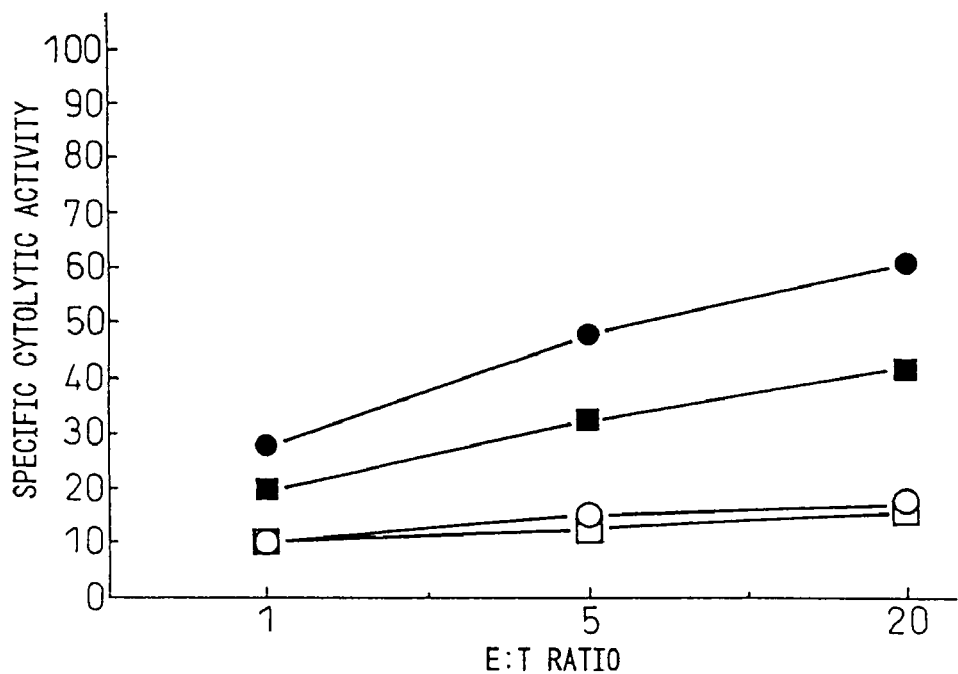
FIG. 1 is a graph showing the cell killing effects (specific cytolytic activity) on C1R2402 target cells (T), either pulsed or not pulsed with peptide, by effecter cells (E) stimulated with WT1 wild peptide (Sequence ID No. 2) or the WT1 modified peptide of the present invention (Sequence ID No. 3). In the graph, the black circles indicate the cytolytic effect on C1R2402 target cells pulsed with wild peptide by effecter cells stimulated with WT1 modified peptide, the black squares indicate the cytolytic effect on C1R2404 target cells pulsed with wild peptide by effecter cells stimulated with WT1 wild peptide, the white circles indicate the cytolytic effect on C1R2402 target cells not pulsed with wild peptide by effecter cells stimulated with WT1 modified peptide, and the white squares indicate the cytolytic effect on C1R2402 target cells not pulsed with wild peptide by effecter cells stimulated with WT1 wild peptide.

The peptide of the present invention is a peptide consisting of 9-30 amino acids that comprises the amino acid sequence consisting of the 9 amino acids shown in Sequence ID No. 3. Moreover, from the viewpoint of being presented by binding to HLA antigen, the peptide is preferably a peptide consisting of 9-12 amino acids that comprises the amino acid sequence shown in Sequence ID No. 3 and, more preferably, is a peptide having rules (motifs) in the sequence of antigen peptide presented by binding to HLA antigen at that time (J. Immunol., 152, p. 3913, 1994; Immunogenetics, 41, p. 178, 1995; J. Immunol., 155, p. 4307, 1994; J. Immunol., 155, p. 4749, 1995). Moreover, the peptide is most preferably a peptide consisting of an amino acid sequence of the 9 amino acids shown in Sequence ID No. 3.

Furthermore, the aforementioned "peptide comprising the amino acid sequence shown in Sequence ID No. 3" is specifically, for example, a peptide comprising the amino acid sequence shown in Sequence ID No. 3 and extending in the direction of the N-terminal and/or the direction of the C-terminal from the applicable position on WT1 (Sequence ID No. 1) (position nos. 235-243) or from the corresponding position on human WT1 (NCBI Database Accession No. XP012009), that has activity as a cancer antigen peptide.

An example of a method for measuring the activity of the cancer antigen peptide of the present invention is the method described in J. Immunol., 154, p. 2257, 1995. The following provides an explanation of an outline of this method using the case of the type of HLA being HLA-A24 as an example. First, peripheral blood lymphocytes are isolated from a person positive for HLA-A24 antigen. Next, by stimulating the peripheral blood lymphocytes by adding the peptide of the present invention in vitro, CTL (cytotoxic T-cells) are induced that specifically recognize the complex of the peptide of the present invention and HLA-A24 presented by the antigen-presenting cells.

This induction of CTL can be investigated by, for example, measuring the amounts of various cytokines (e.g., IFN-γ) produced by the CTL by reacting with the complex of antigen peptide and HLA-A24. In addition, induction of CTL can also be investigated by a method in which the cytotoxicity of the CTL is measured with respect to antigen peptide-presenting cells labeled with $^{51}$Cr or Europium ($^{51}$Cr Release Assay, Int. J. Cancer, 58, p. 317, 1994; Europium Release Assay, J. Immunol., 154, p. 3991, 1995). Moreover, induction of CTL can also be investigated by referring to the examples described later.

The present invention also relates to a cancer vaccine that has the aforementioned antigen as its active ingredient. This vaccine can be used for the prevention or treatment of cancers of the blood such as leukemia, myelodysplastic syndrome, multiple myeloma and malignant lymphoma, as well as solid cancers such as gastric cancer, colon cancer, lung cancer, breast cancer, germinal cell cancer, liver cancer, skin cancer, bladder cancer, prostate cancer, uterine cancer, cervical carcinoma and ovarian cancer. In particular, this vaccine can be applied to patients positive for HLA-A24. This vaccine can be administered orally or parenterally by for example, intraperitoneal, subcutaneous, intracutaneous, intramuscular, intravenous or intranasal administration.

Moreover, administration of the vaccine of the present invention can also be carried out by a method in which monocytes are collected from the peripheral blood of a patient, dendritic cells are extracted from the monocytes, the dendritic cells are pulsed with the peptide of the present invention and then returned to the patient by subcutaneous administration and so forth.

This method is referred to as cytotherapy or dendritic cell (DC) therapy, and the section entitled "Antigen-Presenting Cells" described later should be referred to for further details.

The vaccine, in addition to the peptide administered as the aforementioned active ingredient, may also contain pharmaceutically allowable carriers such as a suitable adjuvant (Clin-Microbiol. Rev., 7, 277-289, 1994), examples of which include a mineral gel like aluminum hydroxide, a surfactant like phosphorous lecithin and a pluronic polyole, a polyanion, a peptide and an oily emulsion. Alternatively, the vaccine may contain other aggregates mixed into liposomes or blended into polysaccharide or the vaccine. The dosage is typically 0.1 μg/kg to 1 mg/kg per day.

In the present invention, DNA that codes the aforementioned polypeptide vaccine can also be used as a vaccine (DNA vaccine). Namely, after inserting nucleic acids, and preferably DNA, that contain nucleic acids that encode the WT1 modified peptide of the present invention into a suitable vector, and preferably an expression vector, cancer immunity can be imparted by administering the vector to an animal. WO 00/6602 or J. Immunol., 160, p. 1717, 1998 and so forth should be referred to for the specific technique used for this DNA vaccine.

In addition, the present invention relates to antigen-presenting cells on which a complex of HLA antigen and the aforementioned peptide is presented. In this example, although potent cell killing activity is observed due to stimulation with the peptide of the present invention, this is the result of the presence of antigen-presenting cells, on which a complex of the peptide of the present invention and HLA antigen (HLA-A24 antigen) is presented, within peripheral blood monocytes, and of the induction of CTL (cytotoxic T-cells) that specifically recognize these antigen-presenting cells. These antigen-presenting cells on which a complex of HLA antigen and the peptide of the present invention is presented are used effectively in cytotherapy (DC therapy) as described below.

The antigen-presenting cells used in cytotherapy are produced by isolating cells having the ability to present antigen from tumor patients, pulsing these cells with peptide of the present invention outside the body, and causing a complex of HLA antigen and the peptide of the present invention to be presented on the surface of the cells. Here, although there are no particular restrictions on the "cells having the ability to present antigen" provided they are cells that express HLA antigen capable of presenting the peptide of the present invention on the surface of the cells, dendritic cells are preferable since they are considered to have high antigen-presenting ability.

In addition, the peptide of the present invention that is used to pulse the aforementioned cells having the ability to present antigen may not only be in the form of a peptide, but rather may also be in the form of DNA or RNA that encodes said peptide.

A specific method for preparing the antigen-presenting cells of the present invention can be referred to in, for example, Cancer Immunol. Immunother., 46, 82, 1998, J. Immunol., 158, p. 1796, 1997, and Cancer Res., 59, p. 1184, 1999. In the case of using dendritic cells, lymphocytes are isolated from the peripheral blood of a tumor patients using the Fycoll method, and after subsequently removing the non-adhered cells, dendritic cells are derived from the adhered cells by culturing in the presence of GM-CSF and IL-4, after which the antigen-presenting cells of the present invention can be prepared by pulsing the dendritic cells by culturing with the peptide of the present invention.

In addition, in the case of preparing the antigen-presenting cells of the present invention by inserting DNA or RNA encoding the peptide of the present invention into the aforementioned cells having the ability to present antigen, insertion can be carried out by referring to, for example, Cancer Res., 56, p. 5672, 1996 or J. Immunol., 161, p. 5607, 1998 in the case of DNA, or by referring to J. Exp. Med., 184, p. 465, 1996 in the case of RNA.

These antigen-presenting cells can be used as the active ingredient of a tumor therapeutic agent. At that time, in order to maintain the stability of the antigen-presenting cells, the treatment agent preferably comprises physiological saline, phosphate-buffered saline (PBS) or medium and so forth. Examples of administration methods include intravenous administration, subcutaneous administration and intracutaneous administration.

Moreover, the present invention also relates to cytotoxic T-cells (CTL) that recognize a complex of HLA antigen and the aforementioned peptide. The CTL of the present invention can be effectively used in the adoptive immunotherapy described below.

Namely, in the case of melanoma, adoptive immunotherapy has been recognized to be therapeutically effective by culturing a large number of the patient's T-cells that have invaded the tumor in vitro, and then returning them to the patient (J. Natl. Cancer Inst., 86, 1159, 1994). In addition, in the case of mouse melanoma, inhibition of metastasis has been observed by stimulating spleen cells in vitro with tumor antigen peptide TRP-2, allowing specific CTL to proliferate in the tumor antigen peptide, and then administering said CTL to melanoma-transplanted mice (J. Exp. Med., 185, 453, 1997). This is based on the result of allowing CTL to proliferate in vitro that specifically recognize a complex of the HLA antigen of antigen-presenting cells and tumor antigen peptide. Thus, a treatment method in which patient peripheral blood lymphocytes are stimulated in vitro using the peptide of the present invention to increase tumor-specific CTL followed by returning these cells to the patient is thought to be useful.

In this manner, the CTL of the present invention can be used as the active ingredient of a tumor therapeutic agent. At that time, in order to maintain the stability of the CTL, the therapeutic agent preferably comprises physiological saline, phosphate-buffered saline (PBS) or medium and so forth. Examples of administration methods include intravenous administration, subcutaneous administration and intracutaneous administration.

The following examples serve to clarify the usefulness of the peptide of the present invention as a cancer antigen and cancer vaccine.

Example 1

Peripheral blood mononuclear cells were isolated from HLA-A*2402-positive donors and distributed among the wells of a 24-well plate at $2 \times 10^6$ cells/well followed by the addition of WT1 wild peptide or WT1 modified peptide to a concentration of 20 µM and culturing for 1 week. The medium used at this time consisted of 45% RPMI, 45% AIV, 10% FCS 1× non-essential amino acids and SM/PCG. Following the aforementioned culturing, the cells were adjusted to $2 \times 10^6$ cells/well and used as responder cells.

On the other hand, other peripheral blood mononuclear cells were similarly isolated from the same HLA-A*2402-positive donors and then peptide-pulsed by culturing for 4 days with one of the aforementioned peptides at 20 µM. After then irradiating at 30 Gy, the cells were adjusted to $4 \times 10^6$ cells/well and used as stimulator cells.

The responder cells and stimulator cells prepared in the manner described above were then mixed and then cultured for 1 week following the addition of IL-2 at 50 U/ml. As a result, the status of the resulting cells were as shown in the following table.

TABLE 1

| Peptide | No. of cells | CD4 | CD8 |
|---|---|---|---|
| WT1 wild peptide | $2.4 \times 10^6$/well | 5% | 35% |
| WT1 modified peptide | $3.0 \times 10^6$/well | 18% | 38% |

Next, a killing assay was carried out in accordance with $^{51}$Cr release method (J. Immunol., 164, 1873, 2000). C1R2402 cells and C1R2402 cells pulsed with the aforementioned peptides were used for the target cells. Cells stimulated by WT1 wild peptide or WT1 modified peptide as previously described (effector cells (E)) were then allowed to act on each of these target cells (T) at an E:T ratio of 1, 5 of 20, followed by measurement of cell lysis. Those results are shown in FIG. 1. As is clear from this graph, cells stimulated with WT1 modified peptide exhibited a more potent cell killing activity than cells stimulated with WT1 wild peptide.

Example 2

The cell killing activity of effector cells stimulated with WT1 wild peptide or WT1 modified peptide on leukemia cells that endogenously express WT1 antigen was tested according to the $^{51}$Cr release method. WT1+/A*2402+ cells (leukemia cells from AML patient #1), WT1−/A*2402+ cells (leukemia cells from AML patient #2), WT1+/A*2402− cells (leukemia cells from AML patient #3) and WT1−/A*2402− cells (leukemia cells from AML patient #4) were used for the target cells.

Figure 2:
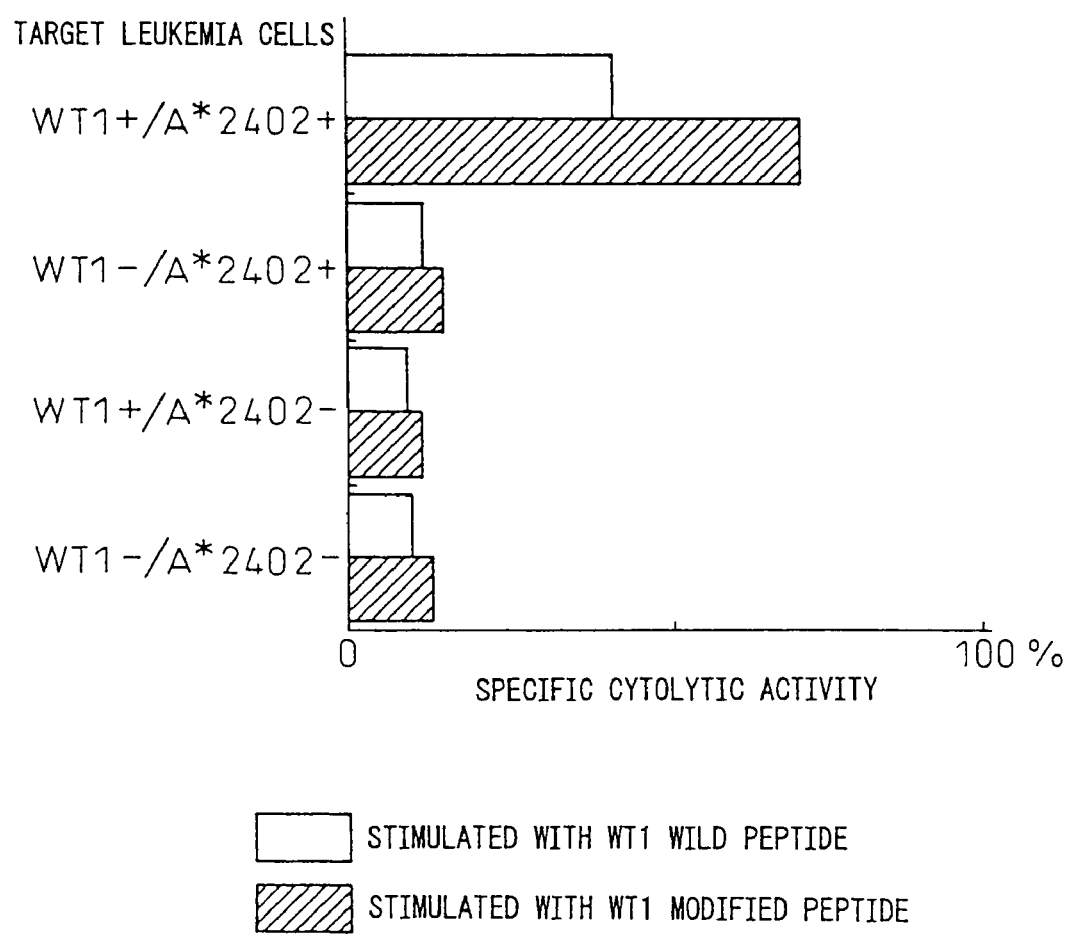
FIG. 2 is a graph showing the cytolytic activity on acute myelocytic leukemia cells endogenously expressing WT1 antigen or on acute myelocytic leukemia cells not expressing WT1 antigen by effecter cells stimulated with WT1 wild peptide or the WT1 modified peptide of the present invention.

The effector cells (E) prepared in Example 1 and the aforementioned target cells (T) were mixed at an E:T ratio of 20:1 and cultured for 4 hours followed by measurement of the degree of cell lysis. Those results are shown in FIG. 2.

As is clear from this graph, although both the cells stimulated with WT1 wild peptide or WT1 modified peptide demonstrated cytotoxic activity on the WT1+/A*2402 cells, the level of that activity was higher for the WT1 modified peptide.

Example 3

Figure 3:
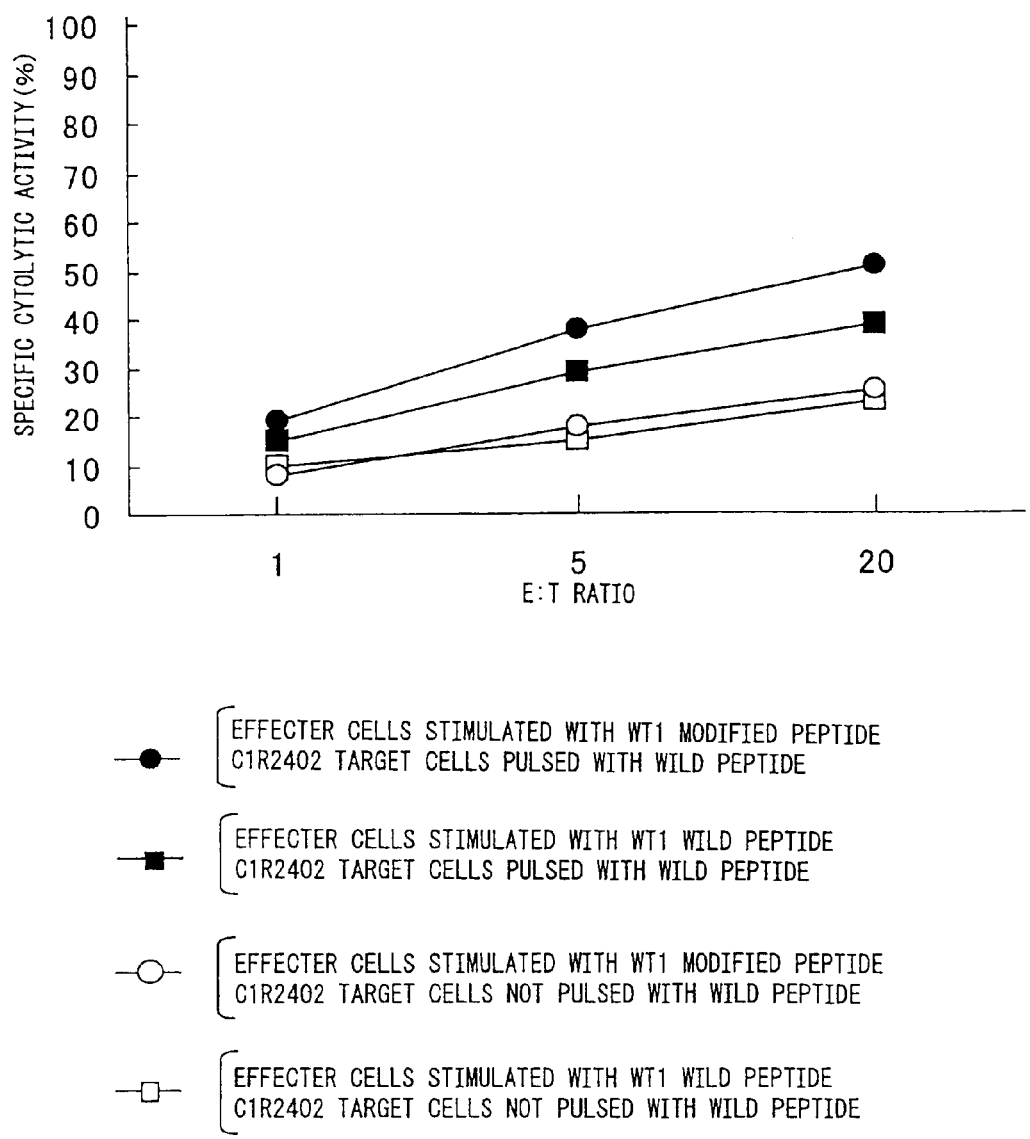
FIG. 3 is a graph showing the cell killing effects (specific cytolytic activity) on C1R2402 target cells, either pulsed or not pulsed with peptide, by effecter cells stimulated with WT1 wild peptide or the WT1 modified peptide of the present invention. In the graph, the black circles indicate the cytolytic effect on C1R2402 cells pulsed with wild peptide by effecter cells stimulated with WT1 modified peptide, the black squares indicate the cytolytic effect on C1R2402 target cells pulsed with wild peptide by effecter cells stimulated with WT1 wild peptide, the white circles indicate the cytolytic effect on C1R2402 target cells not pulsed with wild peptide by effecter cells stimulated with WT1 modified peptide, and the white squares indicate the cytolytic effect on C1R2402 target cells not pulsed with wild peptide by effecter cells stimulated with WT1 wild peptide.

The same experiment as Example 1 was carried out using effector cells prepared from peripheral blood mononuclear cells of different healthy donors positive for HLA-A*2402. Those results are shown in FIG. 3.

As is clear from this graph, similar to Example 1, cells stimulated with WT1 modified peptide exhibited a more potent cytotoxic activity than cells stimulated with WT1 wild peptide.

Example 4

The cytotoxic activity of effector cells stimulated with WT1 wild peptide or WT1 modified peptide was tested on a cancer cell line associated with lung cancer that endogenously expresses WT1 antigen (target cells) using the $^{51}$Cr release method. RERF-LCAI (WT1+/A*2402+), LC1sq (WT1+/A*2402+), 11-18 (WT1−/A*2402+) and LK87 (WT1+/A*2402−) cells were used for the target cells.

Figure 4:
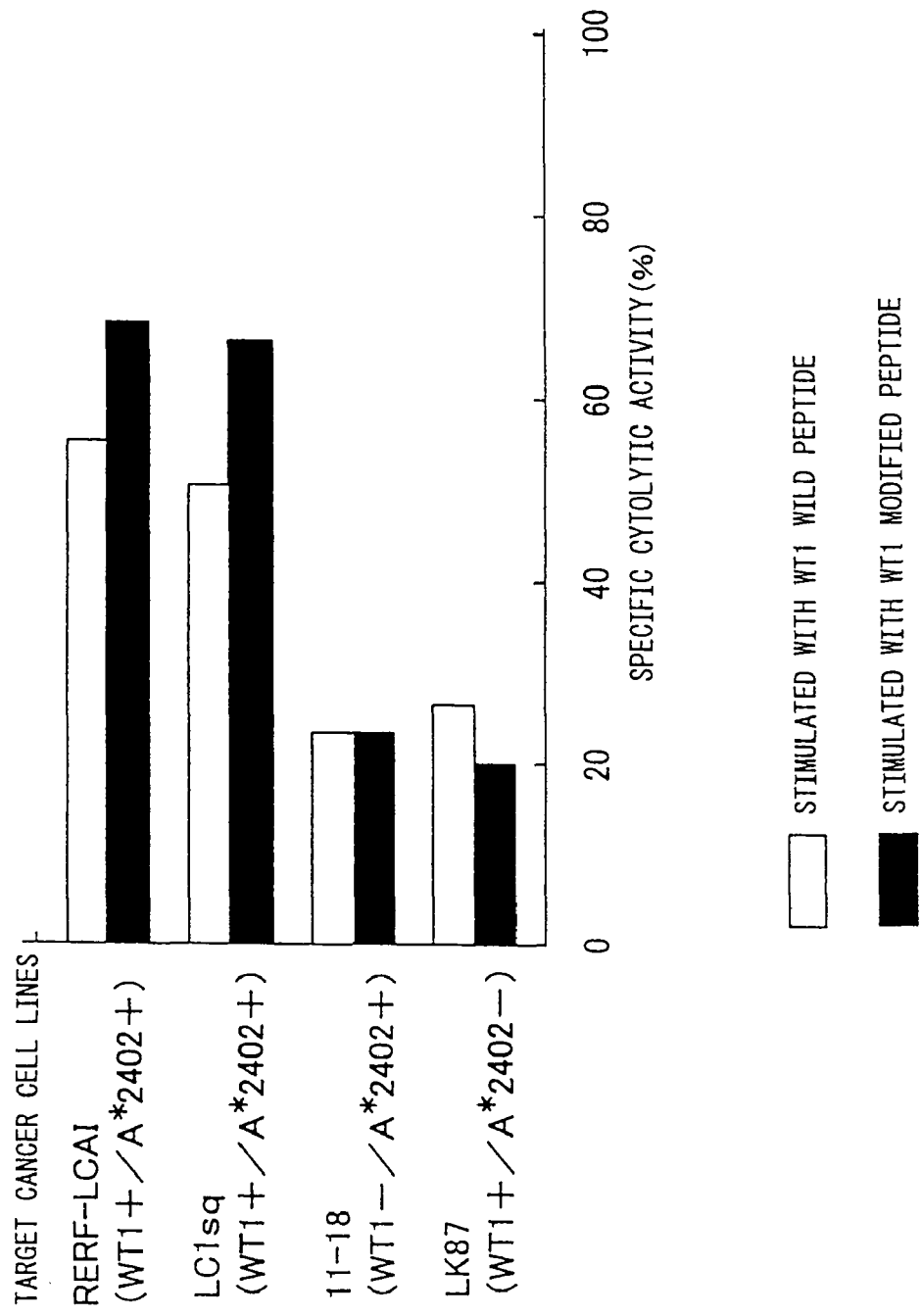
FIG. 4 is a graph showing the cytolytic activity on lung cancer cell lines endogenously expressing WT1 or not expressing WT1 by effecter cells stimulated with WT1 wild peptide or the WT1 modified peptide of the present invention.

Effector cells (E) prepared in the same manner as Example 1 and the aforementioned target cells (T) labeled with $^{51}$Cr were cultured for 4 hours at an E:T ratio of 20:1 in the same manner as Example 2 followed by measurement of the degree of cell lysis. Those results are shown in FIG. 4.

As is clear from this graph, although both the cells stimulated with WT1 wild peptide or WT1 modified peptide demonstrated cytotoxic activity only on the WT1+/A*2402+ cells, the level of that activity was higher for WT1 modified peptide.

Example 5

Figure 5:
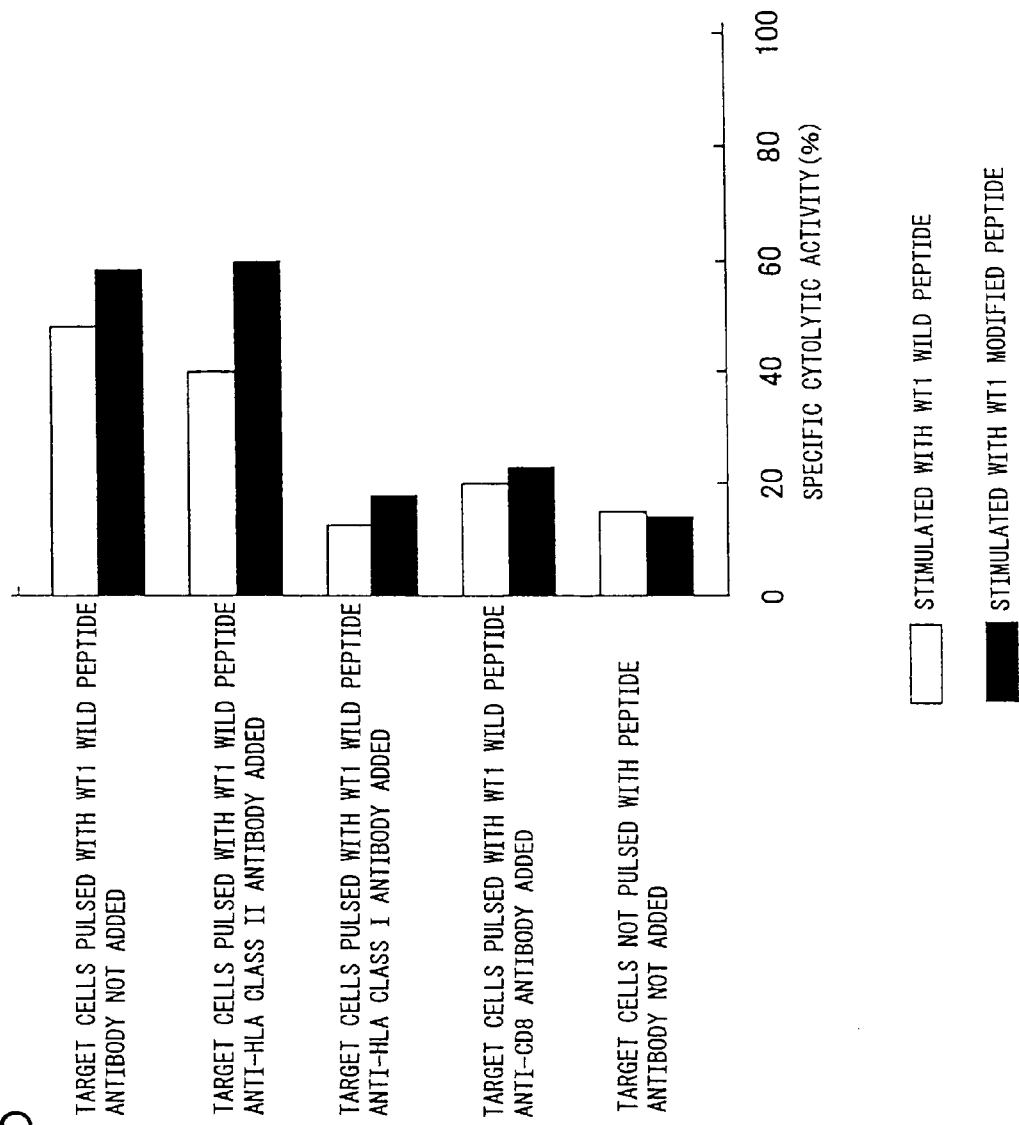
FIG. 5 is a graph showing the inhibitory effects of anti-HLA class I antibody, anti-HLA class II antibody and anti-CD8 antibody on the cell killing effects (specific cytolytic activity) on C1R2402 target cells pulsed with wild peptide by effecter cells stimulated by WT1 wild peptide or the WT1 modified peptide of the present invention.

Effector cells stimulated with WT1 wild peptide or WT1 modified peptide were confirmed to be CD8-positive killer cells that bind to HLA class I by a blocking assay using antibody. The antibodies used consisted of anti-HLA class I antibody, anti-HLA class II antibody and anti-CD8 antibody. Effector cells (E) prepared in the same manner as Example 1 and target cells (T) in the form of C1R2402 cells or C1R2402 cells pulsed with WT1 wild peptide, both labeled with $^{51}$Cr, were mixed with antibody at an E:T ratio of 20:1 and then cultured for 4 hours followed by measurement of the degree of cell lysis according to the $^{51}$Cr release method. Those results are shown in FIG. 5.

As is clear from this graph, cytotoxic activity was blocked by anti-HLA class I antibody and anti-CD8 antibody for both the cells stimulated with WT1 wild peptide or WT1 modified peptide, indicating that the cells that exhibit cytotoxic activity are CD8-positive killer cells that bind to HLA class I.

Example 6

The binding affinity of WT1 modified peptide and WT1 wild peptide to HLA-A*2402 was investigated. After treating C1RA2402 cells for 1 minute with a buffer solution (131 mM citric acid, 66 mM sodium phosphate, 290 m osmol, pH 3.3), the cells were neutralized by adding DMEM medium comprising 0.5% bovine serum albumin. After washing the cells with the medium, they were suspended at a concentration of $2 \times 10^6$ cells/ml in DMEM medium containing 200 nM β2-microglobulin (Sigma) and 0.5% bovine serum albumin. 15 μl of the cell suspension were mixed with 50 μl of the medium comprising various concentrations of WT1 peptide followed by incubating for 4 hours at room temperature. After washing the cells, they were stained with monoclonal antibody to HLA-A24 labeled with FITC (clone name: 7A12), and the amount of HLA-A24 expressed was analyzed with a flow cytometer FACS system. A similar procedure was performed on the antigen peptide of melanoma antigen pmel 15, which has been reported to bind to HLA-A*2402 (Ala Tyr Gly Leu Asp Phe Tyr Ile Leu) (Sequence ID No. 4) (J. Immunol., 154, 5994, 1995), and using this as a standard, the dissociation constants (Kd) of the WT1 peptides were calculated according to the method described in the literature (Immunogenetics, 51, 816, 2000). These results are shown in Table 2.

TABLE 2

| Peptide | Dissociation constant Kd (M) |
| --- | --- |
| WT1 wild peptide | $1.82 \times 10^{-5}$ |
| WT1 modified peptide | $6.40 \times 10^{-7}$ |

As is clear from this table, WT1 modified peptide demonstrated stronger binding affinity for HLA-A*2402 than the WT1 wild peptide.

On the basis of the aforementioned results, the peptide of the present invention was proven to unquestionably function as a cancer antigen, and cause the induction and proliferation of killer T-cells (cancer cell cytotoxic T-cells) against cancer cells. Thus, the cancer antigen peptide of the present invention is useful as a cancer vaccine against leukemia and solid cancers accompanying an increased expression of the WT1 gene.

The invention claimed is:

1. A method for treating a WT-1 expressing cancer, comprising administering an effective amount of a peptide consisting of Cys Tyr Thr Trp Asn Gln Met Asn Leu (SEQ ID NO: 3) to a patient in need thereof.

2. The method of claim 1, wherein the peptide is administered with an adjuvant.

3. The method of claim 1, wherein the peptide is administered with an oily emulsion.

4. The method of claim 1, wherein the patient is positive for HLA-A24.

5. The method of claim 1, wherein the WT-1 expressing cancer is leukemia or solid cancer.

* * * * *